US 6,922,064 B2

(12) United States Patent
Halalay et al.

(10) Patent No.: US 6,922,064 B2
(45) Date of Patent: Jul. 26, 2005

(54) FLUID QUALITY TEST METHOD BASED ON IMPEDANCE

(75) Inventors: Ion C. Halalay, Grosse Pointe, MI (US); Ellen Shirley E. Schwartz, Warren, MI (US)

(73) Assignee: General Motors Corporation, Detroit, MI (US)

( * ) Notice: Subject to any disclaimer, the term of this patent is extended or adjusted under 35 U.S.C. 154(b) by 0 days.

(21) Appl. No.: 10/465,478

(22) Filed: Jun. 18, 2003

(65) Prior Publication Data

US 2004/0257094 A1 Dec. 23, 2004

(51) Int. Cl.$^7$ ............................................. G01R 27/08
(52) U.S. Cl. ........................................ 324/698; 324/663
(58) Field of Search .................. 73/865.5; 324/71.4, 324/446, 632, 639, 642, 643, 692, 698, 663

(56) References Cited

U.S. PATENT DOCUMENTS

| | | | | |
|---|---|---|---|---|
| 5,089,780 A | | 2/1992 | Megerle ..................... 324/448 |
| 5,200,027 A | | 4/1993 | Lee et al. .................... 216/51 |
| 5,274,335 A | | 12/1993 | Wang et al. ................ 324/689 |
| 5,604,441 A | * | 2/1997 | Freese et al. ............... 324/663 |
| 5,644,239 A | | 7/1997 | Huang et al. ............... 324/439 |
| 5,754,055 A | * | 5/1998 | McAdoo et al. ............ 324/636 |
| 5,789,665 A | * | 8/1998 | Voelker et al. ............. 73/53.05 |
| 6,028,433 A | * | 2/2000 | Cheiky-Zelina et al. .... 324/663 |
| 6,278,282 B1 | | 8/2001 | Marszalek ................... 324/663 |
| 6,327,900 B1 | | 12/2001 | Mc Donald et al. ........ 73/117.3 |
| 6,380,746 B1 | * | 4/2002 | Polczynski et al. ......... 324/446 |
| 6,449,580 B1 | | 9/2002 | Bardetsky et al. .......... 702/130 |
| 6,459,995 B1 | | 10/2002 | Collister ..................... 702/23 |
| 6,577,112 B2 | * | 6/2003 | Lvovich et al. ............. 324/71.1 |
| 2002/0125899 A1 | | 9/2002 | Lvovich et al. | |
| 2003/0222656 A1 | * | 12/2003 | Phillips et al. .............. 324/605 |

* cited by examiner

*Primary Examiner*—N. Le
*Assistant Examiner*—Walter Benson
(74) *Attorney, Agent, or Firm*—Kathryn A. Marra

(57) ABSTRACT

A system for determining a quality of a fluid includes an impedance cell immersed in the fluid and impedance instrumentation that communicates with the impedance cell. A controller measures a first impedance of the fluid using an electrical signal at a first frequency, measures a second impedance of the fluid using an electrical signal at a second frequency and measures a third impedance of the fluid using an electrical signal at a third frequency. The controller determines a permittivity and a resistivity of the fluid based on the first, second and third impedances. The quality of the fluid is evaluated based on the permittivity and the resistivity.

22 Claims, 4 Drawing Sheets

FLUID QUALITY TEST METHOD BASED ON IMPEDANCE

FIELD OF THE INVENTION

The present invention relates to fluid quality determination, and more particularly to determining fluid quality based on electrical impedance.

BACKGROUND OF THE INVENTION

Many types of machines use fluids such as oil, lubricant or hydraulic fluid. Exemplary machines include vehicle engines, transmissions or manufacturing machines. The fluid quality plays a significant role in the operation and maintenance of the machine and protection of the machine components. Low grade fluids do not adequately protect machine components and can cause damage due to thermal influences and wear. Used fluids that have broken down through use may cause similar damage to the machine components.

Systems have been developed to monitor the fluid quality of these machines. These systems generally include an impedance cell and corresponding instrumentation that measures the impedance of a fluid sample. In one example, an AC signal having a non-zero DC offset is applied to the fluid through an impedance cell and an AC signal is swept across a frequency range from millihertz (mHz) to megahertz (MHz). The measured impedance is compared to reference impedance values to determine the fluid quality.

Inclusion of a DC offset and the AC sweep across a wide frequency range requires a significant amount of time, as well as equipment that is more complicated and more expensive than is desired. Further, impedance data that is measured with one impedance cell is not comparable to impedance data that is measured with an impedance cell of a different design. This is because the geometry of the impedance cell including the size and physical properties of the electrodes influence the impedance data. As a result, if the impedance cell requires replacement, data that was obtained for a fluid with one type of cell cannot be compared to the data generated by another type of impedance cell.

SUMMARY OF THE INVENTION

Accordingly, the present invention provides a system for determining a quality of a fluid. The system includes an impedance cell immersed in the fluid and impedance instrumentation that communicates with the impedance cell. A controller measures a first impedance of the fluid using an electrical signal at a first frequency, measures a second impedance of the fluid using an electrical signal at a second frequency and measures a third impedance of the fluid using an electrical signal at a third frequency. The controller determines a permittivity and a resistivity of the fluid based on the first, second and third impedances. The quality of the fluid is evaluated based on the permittivity and the resistivity.

In one feature, the system further includes a temperature sensor that communicates with the controller. The temperature sensor is immersed in the fluid and generates a temperature signal. In one embodiment, the controller determines the permittivity and the resistivity at the working temperature of the fluid and converts the permittivity and the resistivity to values corresponding to a reference temperature. In another embodiment, the controller measures the first, second and third impedances when the temperature is equal to a reference temperature.

In another feature, the controller measures a fourth impedance of the fluid using an electrical signal at a fourth frequency and determines the permittivity and the resistivity of the fluid based on the values of the impedance at four frequencies.

In another feature, the second frequency is approximately ten times greater than the first frequency.

In still another feature, the third frequency is approximately ten times greater than the second frequency.

In yet another feature, the fourth frequency is approximately ten times greater than the third frequency.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiments is merely exemplary in nature and is in no way intended to limit the invention, its application, or uses.

Figure 1:
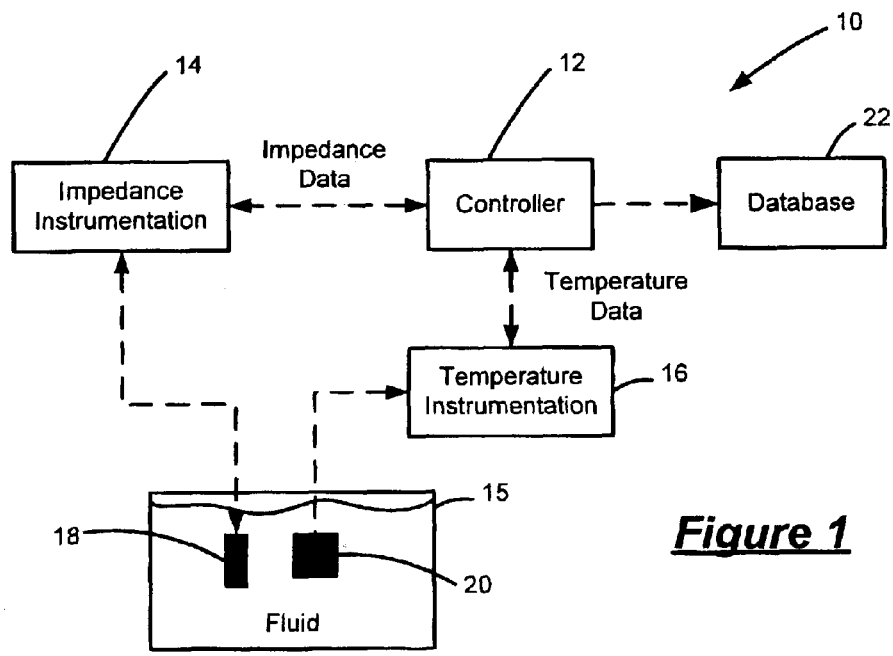
FIG. 1 is a schematic illustration of a system for determining quality of a fluid based on electrical impedance.

Referring now to FIG. 1, a schematic illustration of a system 10 for determining quality of a fluid based on electrical impedance is shown. The present invention anticipates implementation of the system 10 in any type of environment where fluid quality is significant. In one example, the system 10 is incorporated in a vehicle to enable determination of fluid quality for fluids such as engine oil or transmission fluid. Alternatively, the system 10 can be implemented with machine equipment to enable determination of fluid quality for fluid such as lubricant or hydraulic fluid. These two examples are merely illustrative of the various environments in which the system 10 of the present invention can be implemented and are not intended to limit the invention, its applications or uses.

The system 10 includes a controller 12, impedance instrumentation 14 and temperature instrumentation 16. The controller 12 can be in the form of a computer having data acquisition hardware attached thereto and running analysis software programs. It is anticipated, however, that the controller 12 can be any type of computer or controller having input, output, data storage and processing capabilities.

The impedance instrumentation 14 monitors the impedance of a fluid within a reservoir 15 based on a signal from a measuring cell 18. The impedance instrumentation 14 includes a multi-frequency AC generator that applies a periodic electrical signal across the cell 18. The cell 18 sends a response signal to the impedance instrumentation, which uses the signal to determine the impedance of the fluid. Exemplary impedance instrumentation includes an auto-balancing AC bridge, an LCR meter or any other suitable device.

The temperature instrumentation 16 monitors the temperature of the fluid based on a signal from a temperature sensor 20. Exemplary temperature sensors include a thermistor, a thermocouple or any other suitable sensor. The temperature may also be derived from other known parameters. The temperature instrumentation 16 is dependent upon the type of temperature sensor 20 that is used. In the case of a thermistor, the temperature instrumentation 16 includes an ohmmeter. In the case of a thermocouple, the temperature instrumentation 16 includes a voltmeter. The temperature instrumentation 16 sends a temperature signal to the controller 12.

Virtually all fluids are able to pass current when a voltage is applied. For different types of fluid, the impedance $Z(f)$ varies with the frequency of the applied voltage and the properties of the fluid. The impedance $Z(f)$ is a complex function that can be represented with either Cartesian components as $Z(f)=Z'(f)+i\, Z''(f)$ or with polar components as $Z(f)=|Z(f)|e^{i\theta(f)}$. $Z'(f)$ is the real part of the impedance function $Z(f)$ and $Z''(f)$ is the imaginary part. $|Z(f)|$ is the modulus or amplitude of $Z(f)$ and $\theta(f)$ is the phase angle. It should be noted that the components of $Z(f)$, whether Cartesian or polar, are functions of frequency.

Figure 2:
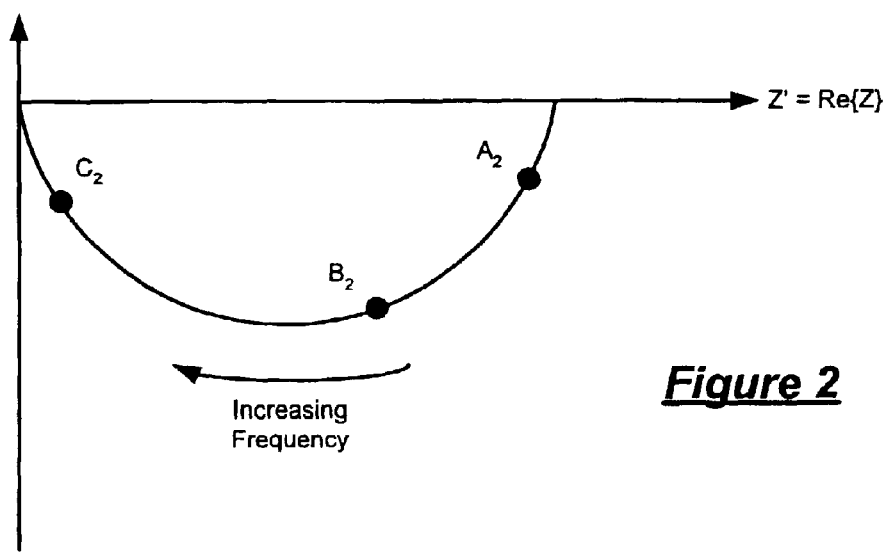
FIG. 2 is a Nyquist plot illustrating a 3-point impedance curve based on impedance measurements at three frequencies.
Figure 3:
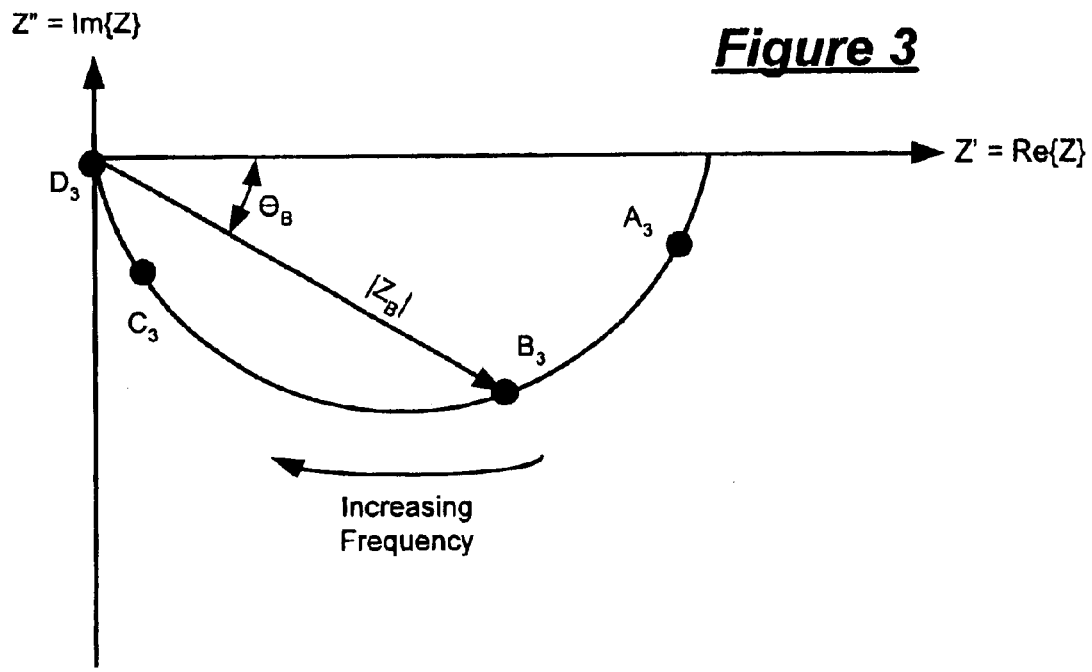
FIG. 3 is a Nyquist plot illustrating a 4-point impedance curve based on impedance measurements at four frequencies.

Referring now to FIGS. 2 and 3, a representation of $Z(f)$ is made by plotting $Z''$ versus $Z'$. The plots of FIGS. 2 and 3 are called Nyquist plots in electrical engineering and Argand diagrams in mathematics. It should be noted that the frequency dependence on a Nyquist is implicit. That is to say that each point of the curve corresponds to a different frequency. Plots of the polar components $|Z(f)|$ and $\theta(f)$ of $Z(f)$ versus frequency are known as Bode plots (see FIGS. 5A and 5B, discussed in detail below).

The plot of FIG. 2 includes individual data points $A_2$, $B_2$ and $C_2$ that correspond to $Z(f)$ measurements at three different frequencies. The curve of the Nyquist plot can be determined using only the three data points. The plot of FIG. 3 includes individual data points $A_3$, $B_3$, $C_3$ and $D_3$ that correspond to $Z(f)$ measurements at four different frequencies. The curve of the Nyquist plot of FIG. 3 is determined more accurately than that of FIG. 2 because it is defined using more data points. Although multiple data points provide a more accurate representation of the $Z(f)$ behavior of the fluid, more time and complex equipment are required. Even though the $Z(f)$ behavior can be determined using only three data points (FIG. 2), a more acceptable accuracy is achievable by determining at least four data points (FIG. 3).

Figure 4:
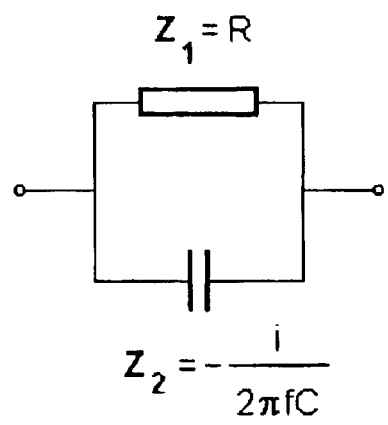
FIG. 4 is a schematic illustration of an equivalent circuit for fitting the electrical impedance of a liquid inside a measurement cell.
Figure 5:
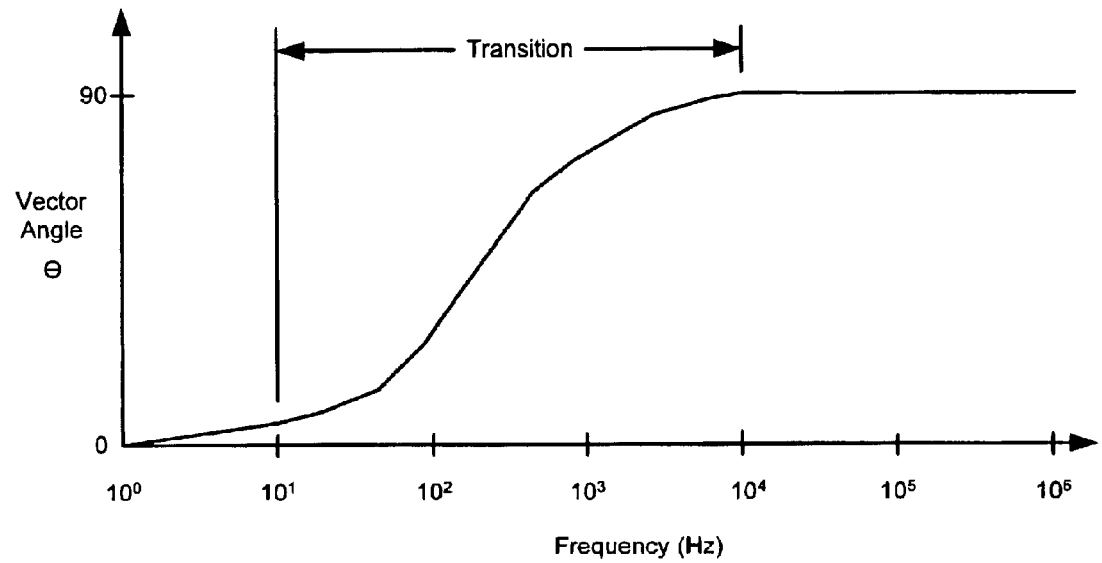
FIG. 5 is a graph of the vector angle versus frequency with associated transition region according to the teachings of the present invention.

The impedance response of a liquid-filled measurement cell 18 comprises two components. One component results from the liquid $Z_{LIQUID}(f)$ and another component results from interfaces between the liquid and the electrodes, $Z_{INTERFACE}(f)$. For any class of fluids, a judicious design of the measurement cell will result in a separation of these two components. In other words, the $Z_{LIQUID}(f)$ and $Z_{INTERFACE}(f)$ components will have significant values in completely separate frequency intervals. The circuit of FIG. 4 is an equivalent circuit that models the impedance response of most fluids of practical interest.

Physical properties of the fluid, such as its electrical permittivity $\epsilon_r$ and electrical resistivity $\rho$ or alternatively its electrical conductivity $K=1/\rho$ can be determined based on the measured impedance $Z(f)$. These properties are independent of the physical structure of the particular cell used to determine $Z(f)$. That is to say, these physical properties of the fluid that are determined using one type of cell 18 are comparable to the physical properties of the fluid that are determined using another type of cell 18. The RC-circuit includes an ohmic resistance (R) and a capacitor (C) connected in parallel. The corresponding impedances of the RC-circuit elements are provided as:

$$Z_1 = R$$

$$Z_2 = -\frac{i}{2\pi f C}$$

where f is the frequency of the AC signal and $i=\sqrt{-1}$.

The AC impedance vector for the RC-circuit is provided as:

$$\frac{1}{Z} = \frac{1}{Z_1} + \frac{1}{Z_2} = \frac{1}{R} - i2\pi f C$$

Using this equation, the modulus or amplitude of the impedance is provided as:

$$|Z| = \frac{1}{\sqrt{\frac{1}{R^2} + 4\pi^2 f^2 C^2}}$$

and its phase angle $\theta$ as:

$$\tan\theta = -2\pi f R C$$

As illustrated in FIG. 3, the $Z(f)$ vector can be plotted and is defined by its amplitude $Z(f)=|Z(f)|$ and phase angle $\theta(f)$. The impedance $Z(f)$ of the cell is measured by determining the amplitude $|Z(f)|$ and the phase angle $\theta(f)$ as described above, for varying frequencies. Preferably, $Z(f)$ is measured using four different frequencies that are separated by a decade, as explained in further detail below. The exemplary data points $A_3$, $B_3$, $C_3$ and $D_3$ indicate the four measured $Z(f)$ values. Although only one is illustrated in FIG. 3, a $Z(f)$ vector with its corresponding magnitude $|Z(f)|$ and phase angle $\theta(f)$ is associated with each data point.

Figure 5A:
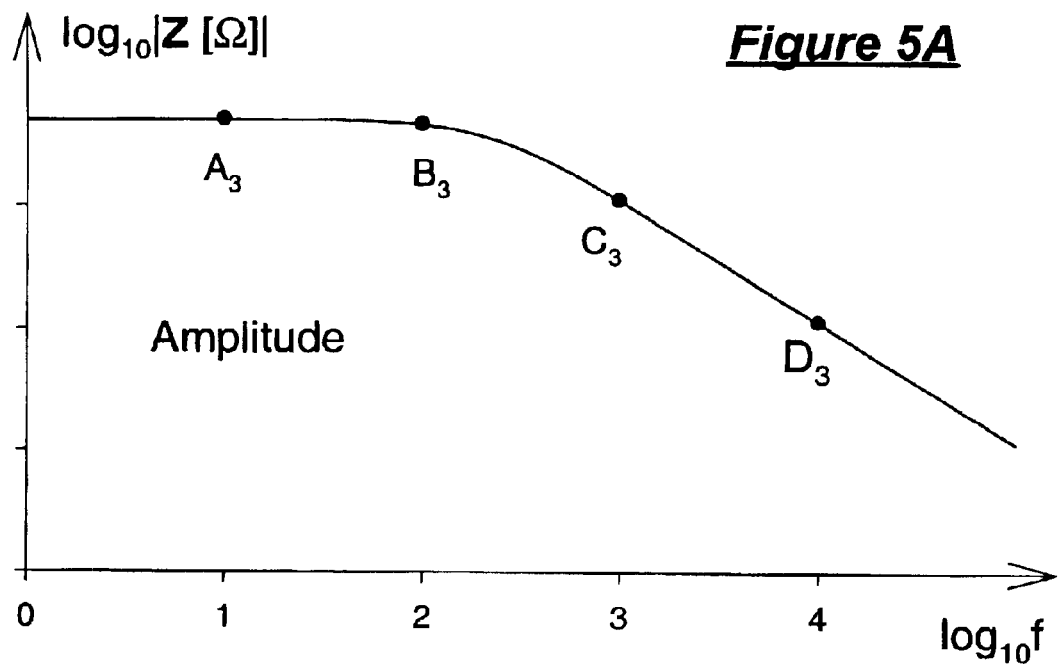
FIG. 5A is a graph of the polar impedance amplitude versus frequency.
Figure 5B:
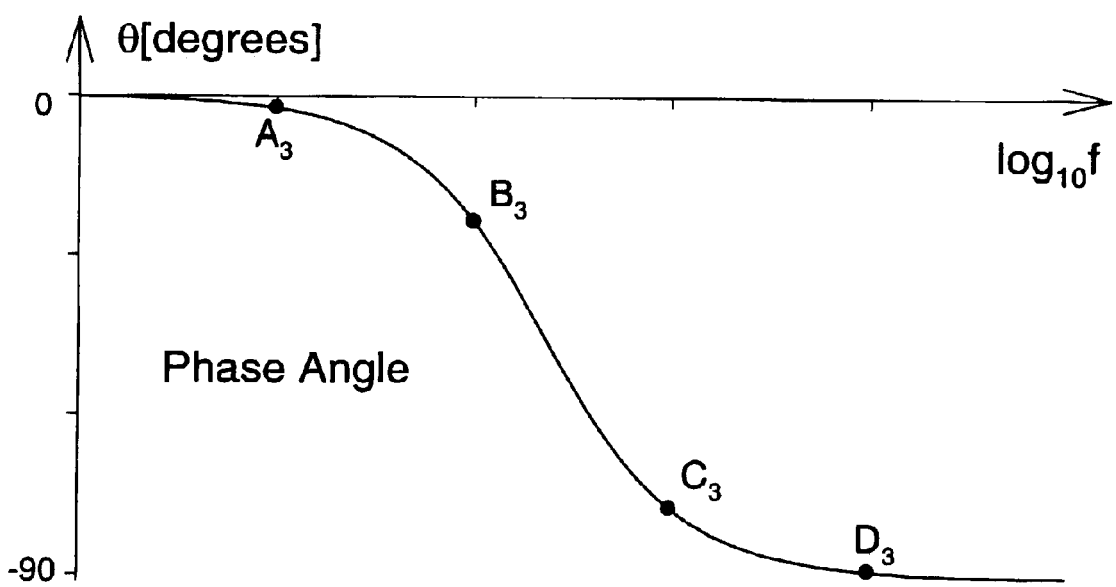
FIG. 5B is a graph of the polar impedance phase angle versus frequency.

Referring now to FIGS. 5A and 5B, plots of the amplitude $|Z(f)|$ and phase angle $\theta(f)$ versus frequency are respectively shown. The S-shaped portion of the $\theta(f)$ plot is also known as the dispersion region and corresponds to the semicircle depicted on the Nyquist plots in FIGS. 2 and 3. This region contains most of the information about the circuit elements that model the impedance response of the liquid. In order to adequately cover this portion of the plot (i.e. be able to determine the semicircles from FIGS. 2 and 3), the Z measurements are taken at the four different frequencies, separated by some amount. In one example, the four frequencies are separated by decades. That is to say, the second frequency is greater than the first frequency by a factor of ten, the third frequency is greater than the second by a factor of ten (i.e., greater than the first frequency by a factor of 100) and the fourth frequency is greater than the third by a factor of ten (i.e., greater than the first frequency by a factor of 1000). In this manner, Z(f) is measured across at least a large portion of the dispersion region.

The controller 12 receives the impedance data and determines both R and C using pre-programmed mathematical models and data fitting techniques. More particularly, R and C of the fluid remain constant and the impedance varies with frequency. Using the four data points, the controller 12 performs a curve fit and determines the constants R and C. Having determined R and C, the controller 12 calculates the permittivity and resistivity of the fluid. The electrical resistivity $\rho$ and the electrical permittivity $\epsilon_r$ are physical properties of the fluid in its current state and are independent of the type of cell 18 or cell geometry used to measure the impedance Z(f). Alternatively, one may use in the analysis the electrical conductivity $\sigma$ and electrical permittivity $\epsilon_r$ of the fluid, since the resistivity and conductivity are quantities that are the reciprocal to each other (i.e., $\rho=1/\sigma$). The resistivity is directly related to R and the electrical permittivity is directly related to C, respectively, through the relations $\epsilon_r=C/C_g$ and $\rho=R/K$, where $C_g$ and K are the geometrical capacitance of the cell and the cell conductivity constant, respectively.

Figure 6:
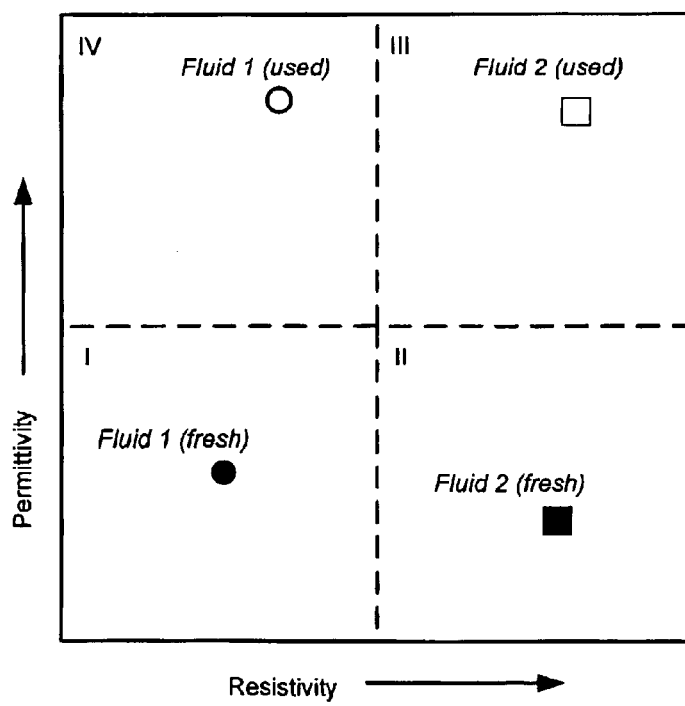
FIG. 6 is a plot of permittivity versus resistivity for an exemplary fluid type.

Referring now to FIG. 6, a resistivity versus permittivity plot for the exemplary fluid of oil is shown. For the exemplary fluid, resistivity of the fluid increases based on the fluid properties. That is to say, a lower grade of fluid displays a higher resistivity. For example, a new sample of a high grade fluid has a lower resistivity than a new sample of a lower grade fluid. Similarly, the permittivity of the fluid increases as the fluid breaks down through use. For example, a new sample of a high grade fluid has a lower permittivity than a used sample of the same high grade fluid.

The plot of FIG. 6 is broken up into four quadrants I, II, III and IV. Quadrant I indicates a fresh sample of a high grade fluid and quadrant II indicates a fresh sample of a low grade fluid. Quadrant III indicates a used sample of low grade fluid and quadrant IV indicates a used sample of high grade fluid. For example, Fluid 1 is a high grade fluid. A fresh sample of Fluid 1 is indicated in quadrant I. As Fluid 1 breaks down through usage, its quality decreases as indicated in quadrant IV. Similarly, Fluid 2 is a low grade fluid. A fresh sample of Fluid 2 is indicated in quadrant II. As Fluid 2 breaks down through usage, its quality decreases as indicated in quadrant III.

Temperature significantly influences the resistivity $\rho$ and electrical permittivity $\epsilon$ of a fluid and thus, the parameters R and C of the fluid-filled impedance cell. Therefore, the controller 12 records the temperature of the fluid while the impedance measurements are taken. As a result, the controller 12 determines the permittivity and resistivity of the fluid at the measured temperature. Using this information, the controller 12 converts the resistivity and permittivity of the fluid to a reference temperature. Alternatively, however, the controller 12 can monitor the temperature until the fluid achieves the reference temperature. The controller 12 then measures the fluid impedance at a reference temperature to determine the resistivity and permittivity as explained above.

The values of the resistivity and permittivity at the reference temperature are used to determine the fluid quality. More particularly, the measured values of resistivity and permittivity are compared to historical values stored in a database 22 (see FIG. 1). The database 22 is accessible by the controller 12. The resistivity and permittivity are compared to previously determined fresh and used values on the plot to determine the fluid quality. In simpler terms, the previously determined values define the boundaries of the quadrants I, II, III and IV of the resistivity versus permittivity plot for any given class of liquids.

As the fluid quality is monitored by the system 10, the database 22 of resistivity and permittivity information continuously grows. Using this database, the controller 12 is able to quickly compare the current resistivity and permittivity information to that previously measured in order to more accurately determine the quality of the fluid. As the database grows, the accuracy of the fluid quality determination is improved.

As discussed briefly above, permittivity and resistivity are physical properties of the fluid and are independent of the particular impedance cell. As a result, the same database can be used for fluid quality determination regardless of the type of impedance cell used. This provides significant advantages over prior art methods. For example, if the cell of a system is replaced, the fluid quality information based on the new cell is still comparable to the information in the database built with data collected by the replaced cell. As another example, the data of an application implementing the system with a particular type of cell is comparable to the data of another application implementing the system with a different type of cell. In this manner, an overall database can be built importing data from numerous other systems. That is to say, a manufacturer can import the databases of any number of systems used in the field to build a central database.

As discussed briefly above, the system 10 can be implemented in any number of applications where fluid quality plays a significant role. Regardless of the type of application, the system 10 can be used in at least three roles. In one role, the system 10 is used to monitor the fluid as the fluid degrades through use. By monitoring degradation of the fluid, the system 10 can provide an alert to an operator that the fluid has degraded to a point where it should be changed to avoid damage to other components of the particular application.

In another role, the system 10 is used is to monitor the grade of fluids being introduced into the application. For example, an operator could introduce a low grade fluid into the application for a number of reasons including cutting costs or lack of availability of a higher grade fluid. The system 10 immediately recognizes the presence of a sub-standard fluid and can alert the operator, store the condition in memory or both. In the event that an application experiences problems, such as a breakdown, maintenance personnel can readily retrieve the fluid quality information from the controller's memory. Using this information, the maintenance personnel can determine whether the problem was the result of neglect (i.e., not changing the fluid as it degrades), misuse (i.e., using sub-standard fluid) or some other reason. As a result, a manufacturer could reduce warranty claims by identifying instances of neglect or misuse that resulted in the problem.

In yet another role, the system 10 is used for fault finding and troubleshooting of mechanical devices based on the presence of likely contaminants. The electrical permittivity of fluids ranges from approximately 2 to 4 for hydrocarbons, approximately 72 for water, to well above 100 for various nitrogen compounds. Introduction of salt in a liquid can change its resistivity by as much as 10 orders of magnitude. For example, in a marine application, contamination of the engine oil by salt water would cause large changes in both the electrical permittivity and the resistivity determined by the system 10, which would be indicative of one or more failed seals.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A system for determining a quality of a fluid, comprising:

an impedance cell immersed in said fluid;

impedance instrumentation that communicates with said impedance cell; and a controller that measures a first impedance of said fluid using an electrical signal at a first frequency, measures a second impedance of said fluid using an electrical signal at a second frequency, measures a third impedance of said fluid using an electrical signal at a third frequency, determines a permittivity and a resistivity of said fluid independent of said impedance cell and based on said first, second and third impedances and evaluates said quality of said fluid based on said permittivity and said resistivity.

2. The system of claim 1 further comprising a temperature sensor that communicates with said controller, that is immersed in said fluid and that generates a temperature signal.

3. The system of claim 2 wherein said controller determines said permittivity and said resistivity by converting values of said permittivity and said resitivity based on said temperature signal to a reference temperature.

4. The system of claim 2 wherein said controller measures said first, second and third impedances when said temperature is equal to a reference temperature.

5. The system of claim 1 wherein said controller measures a fourth impedance of said fluid using an electrical signal at a fourth frequency and determines said permittivity and said resistivity of said fluid based on said fourth impedance.

6. The system of claim 1 wherein said second frequency is approximately ten times greater than said first frequency.

7. The system of claim 1 wherein said third frequency is approximately ten times greater than said second frequency.

8. The system of claim 5 wherein said fourth frequency is approximately ten times greater than said third frequency.

9. A method of determining quality of a fluid, comprising:

measuring a first impedance of said fluid using a signal having a first frequency;

measuring a second impedance of said fluid using a signal having a second frequency;

measuring a third impedance of said fluid using a signal having a third frequency;

determining a permittivity and a resistivity of said fluid independent of an impedance measuring cell and based on said first, second and third impedances; and evaluating said quality of said fluid based on said permittivity and said resistivity.

10. The method of claim 9 further comprising measuring a fourth impedance of said fluid using a signal at a fourth frequency, wherein said permittivity and said resistivity of said fluid are further based on said fourth impedance.

11. The method of claim 9 wherein said second frequency is approximately ten times greater than said first frequency.

12. The method of claim 9 wherein said third frequency is approximately ten times greater than said second frequency.

13. The method of claim 10 wherein said fourth frequency is approximately ten times greater than said third frequency.

14. The method of claim 9 further comprising measuring a temperature of said fluid.

15. The method of claim 14 further wherein said step of determining said permittivity and said resistivity includes converting values of said permittivity and said resitivity based on said temperature and a reference temperature.

16. The method of claim 14 wherein said steps of measuring said first, second and third impedances are performed when said temperature is equal to a reference temperature.

17. A method of monitoring usage of equipment having a fluid circulated therethrough, comprising:

measuring a first impedance of said fluid using a signal having a first frequency;

measuring a second impedance of said fluid using a signal having a second frequency;

measuring a third impedance of said fluid using a signal having a third frequency;

determining a permittivity and a resistivity of said fluid independent of an impedance measuring cell and based on said first, second and third impedance, and said temperature;

evaluating a quality of said fluid based on said permittivity and said resistivity; and determining whether said equipment was improperly maintained based on said quality.

18. The method of claim 17 further comprising alerting a user of a low quality condition.

19. The method of claim 17 wherein said quality is a grade of said fluid.

20. The method of claim 17 wherein said quality is a degradation level of said fluid.

21. The method of claim 17 wherein said equipment is improperly maintained by non-replacement of said fluid when said quality has degraded to an unacceptable level.

22. The method of claim 17 wherein said equipment is improperly maintained by introduction of a low quality fluid into said equipment.

* * * * *